United States Patent
Xu et al.

(10) Patent No.: US 11,447,746 B2
(45) Date of Patent: Sep. 20, 2022

(54) METHOD FOR INDUCING AMPLIFICATION OF TYPE I NKT CELLS IN VITRO

(71) Applicant: Shanghai Innovative Chang'An Biological Technology Co., Ltd., Shanghai (CN)

(72) Inventors: Jianqing Xu, Shanghai (CN); Xiaoyan Zhang, Shanghai (CN); Jing Wang, Shanghai (CN); Lingyan Zhu, Shanghai (CN)

(73) Assignee: Shanghai Innovative Chang'An Biological Technology Co., Ltd., Shanghai (CN)

( * ) Notice: Subject to any disclaimer, the term of this patent is extended or adjusted under 35 U.S.C. 154(b) by 527 days.

(21) Appl. No.: 16/461,851

(22) PCT Filed: Nov. 1, 2017

(86) PCT No.: PCT/CN2017/108915
§ 371 (c)(1),
(2) Date: May 17, 2019

(87) PCT Pub. No.: WO2018/095204
PCT Pub. Date: May 31, 2018

(65) Prior Publication Data
US 2019/0367875 A1    Dec. 5, 2019

(30) Foreign Application Priority Data
Nov. 22, 2016    (CN) .......................... 201611031666.9

(51) Int. Cl.
*C12N 5/0783*    (2010.01)

(52) U.S. Cl.
CPC ........ *C12N 5/0638* (2013.01); *C12N 2500/30* (2013.01); *C12N 2501/2302* (2013.01); *C12N 2501/2307* (2013.01); *C12N 2501/2312* (2013.01); *C12N 2501/2315* (2013.01); *C12N 2502/1121* (2013.01)

(58) Field of Classification Search
None
See application file for complete search history.

(56) References Cited

U.S. PATENT DOCUMENTS

| | | | |
|---|---|---|---|
| 2004/0009594 A1* | 1/2004 | Wakasugi | C12N 5/0646 435/372 |
| 2013/0157364 A1 | 6/2013 | Hong et al. | |
| 2016/0008460 A1 | 1/2016 | Knolle et al. | |
| 2017/0029777 A1* | 2/2017 | Pillai | C12N 5/0646 |
| 2020/0163992 A1* | 5/2020 | Metelitsa | C12N 5/0646 |

FOREIGN PATENT DOCUMENTS

| | | |
|---|---|---|
| CN | 102168068 A | 8/2011 |
| CN | 102978160 A | 3/2013 |
| CN | 103080302 A | 5/2013 |
| CN | 104357391 A | 2/2015 |
| CN | 104450616 A | 3/2015 |
| CN | 104711225 A | 6/2015 |
| CN | 105154401 A | 12/2015 |
| CN | 105451766 A | 3/2016 |
| CN | 105462924 A | 4/2016 |
| CN | 106434556 A | 2/2017 |
| EP | 1916310 A1 | 4/2008 |
| WO | WO-2009/062001 A1 | 5/2009 |

OTHER PUBLICATIONS

Bernin et al., The cytokine profile of human NKT cells and PBMCs is dependent on donor sex and stimulus, Med. Microbiol. Immunol., 205:321-32 (2016).
Huang et al., Modulation of cytokine-producing of Valpha24 natural killer T cells, J. Clin. Hematology, 21(5):264-7 (May 2008).
International Application No. PCT/CN2017/108915, International Search Report and Written Opinion, dated Jan. 31, 2018.
Chinese Patent Application No. 201611031666.9, Office Action, dated Mar. 27, 2019.
Chinese Patent Application No. 201710034922.8, Office Action, dated Apr. 11, 2019.
Wang et al., CD3/CD28 In vitro expansion of peripheral blood T lymphocytes by immuno magnetic beads, Chin. J. Cell. Mol. Immunol., 30(10):1090-2 (2014).

* cited by examiner

*Primary Examiner* — Michail A Belyavskyi
(74) *Attorney, Agent, or Firm* — Marshall, Gerstein & Borun LLP

(57) ABSTRACT

The present invention relates to a method for inducing amplification of human type I NKT cells in vitro using a "specific stimulant+staged cytokine" mode, which consists of two culture stages, wherein the first culture stage focuses on specific amplification of the number of the type I NKT cells, in which a specific stimulant α-GalCer is used to advantageously amplify the type I NKT cells and α-GalCer-loaded CD1d-expressing cells are used to stimulate continuous proliferation of the type I NKT cells while adding cytokines IL-2 and IL-7 to assist growth of the type I NKT cells; and the second culture stage is to synchronously perform amplification of the number of the type I NKT cells and guide directed function differentiation, in which CD1d-expressing cells incubated with α-GalCer continue to stimulate proliferation of the type I NKT cells while adding IL-2, IL-7 and IL-15 to assist amplification of the type I NKT cells and guide differentiation, and IL-12 is added to the culture system 1-2 days before the end of culture to guide further directed differentiation of the type I NKT cells and enhance their killing activity. The method of the present invention is simple to operate, can greatly amplify the type I NKT cells in vitro while improving the killing activity of the amplification products, and is suitable for large-scale production.

9 Claims, 2 Drawing Sheets

METHOD FOR INDUCING AMPLIFICATION OF TYPE I NKT CELLS IN VITRO

TECHNICAL FIELD

The present invention belongs to the field of cell biology, and particularly relates to a method for inducing amplification of human type I NKT cells in vitro.

BACKGROUND ART

Natural killer T cells (NKT cells) belong to a heterogeneous cell population with the reaction characteristics of innate and adaptive immunity, i.e. NKT cells recognize antigens by specific T cell receptor (TCR) like T cells, specifically recognize lipid antigens presented by a MHC-like molecule CD1d, and can also respond rapidly like natural killer cells (NK cells) to kill target cells. Meanwhile, NKT cells also produce a series of cytokines and chemokines, thus to play an important role in immunoregulation and participate in immune responses against tumors, infections as well as autoimmune diseases.

NKT cells are independent cell populations, different from T cells and NK cells on the cell surface receptors, antigen recognition properties as well as effector ability. Human NKT cells are mainly CD4+ cell populations followed by CD4-CD8-cell populations and CD8+ cell populations. NKT cells are classified into type I NKT cells and type II NKT cells according to the type of TCRs expressed by cells. Type I NKT cells are also known as invariant NKT (iNKT) cells, due to the expression of an invariant TCR, and play an important role in anti-tumor and anti-infective immune responses of the body. Type II NKT cells mainly exert immunoregulatory effects by secreting various cytokines.

Type I NKT cells can specifically recognize lipid antigens presented by CD1d, with α-galactosylceramide (α-GalCer or KRN7000) being the most effective stimulant. Type I NKT cells can respond rapidly after recognizing antigens and directly kill target cells by secreting perforin and granzyme; and assist the activation and proliferation of CD8+T cells, NK cells and DC cells by secreting various cytokines including IFN-γ, IL-5, IL-2, GM-CSF, etc., and promote the development of an adaptive immune response to a Th1-type immune response. Different from type I NKT cells, type II NKT cells do not recognize α-GalCer, and mainly exert immunoregulatory effects by secreting IFN-γ and IL-4 etc, thereby inhibiting anti-tumor, anti-infective immune responses of the body.

Based on in-depth studies on their functions, NKT cells have received attention in the anti-tumor, anti-infective and autoimmune disease treatment fields. However, due to greater differences in the functions of the two types of NKT cells, in order to fully exert their respective advantages, it is particularly important to achieve their respective specific amplification. In particular, when NKT cells are to be used in the anti-tumor and anti-infective fields, the strategy of specifically amplifying type I NKT cells can further improve the killing activity of the amplification products on target cells, which has positive significance on improving the therapeutic effects.

SUMMARY OF THE INVENTION

A technical problem to be solved by the present invention is as follows:

an in-vitro amplification method of type I NKT cells is established to greatly amplify the type I NKT cells while improving their level of excreting effector cytokines and their ability to kill target cells.

To solve the above technical problem, the present invention employs the following technical solution: the entire cell amplification process consists of two culture stages, wherein the first culture stage focuses on specific amplification of the number of the type I NKT cells, in which a specific stimulant α-GalCer is used to advantageously amplify the type I NKT cells and α-GalCer-loaded CD1d-expressing cells are used to stimulate continuous proliferation of the type I NKT cells while adding a cytokine to assist growth of the type I NKT cells, the cytokine comprising at least one of IL-2 and IL-7; and the second culture stage is to synchronously perform amplification of the number of the type I NKT cells and guide directed function differentiation, in which CD1d-expressing cells incubated with α-GalCer continue to stimulate proliferation of the type I NKT cells while adding IL-2, IL-7 and IL-15 to assist amplification of the type I NKT cells and guide differentiation, then adding IL-12 to the culture system 1-2 days before the end of culture to guide further directed differentiation of the type I NKT cells.

Wherein, the CD1d-expressing cells comprise dendritic cells (DCs) and other cells capable of expressing CD1d and/or other artificially modified DC-like antigen presenting cells.

The two culture stages mainly comprise the steps of:
(1) resuspending and adjusting the concentration of peripheral blood mononuclear cells (PBMCs), and adding α-GalCer to culture the type I NKT cells;
(2) on the $7^{th}$ day of culture, adding α-GalCer-loaded DCs to the type I NKT cell culture system while adding IL-2 and IL-7, and maintaining the concentration of α-GalCer in the type I NKT cell culture system unchanged;
(3) on the $14^{th}$ day of culture, re-adding the α-GalCer-loaded DCs to the type I NKT cell culture system while adding IL-15, and maintaining the concentration of α-GalCer, IL-2 and IL-7 in the culture system unchanged;
(4) on the $20^{th}$ day of culture, adding IL-12 to the culture system while maintaining the concentration of α-GalCer, IL-2, IL-7 and IL-15 in the system unchanged, and collecting cells on the $21^{st}$ day of culture.

The α-GalCer-loaded DCs are prepared by resuspending and adjusting the concentration of PBMCs, adding IL-4 and GM-CSF with working concentrations of 500 U/ml and 50 ng/ml respectively to induce differentiation of DCs, and on the $6^{th}$ day of culture, adding α-GalCer to the DC culture system for pre-incubation for 24 h.

In addition, the initial concentration of the PBMCs for culturing the type I NKT cells is from $5 \times 10^5$ cells/ml to $3 \times 10^6$ cells/ml and the initial concentration of the PBMCs for inducing the differentiation of the DCs is from $1 \times 10^6$ cells/ml to $5 \times 10^6$ cells/ml. The α-GalCer has a working concentration of from 50 ng/ml to 500 ng/ml; the IL-2 has a working concentration of from 10 U/ml to 100 U/ml, the IL-7 has a working concentration of from 20 ng/ml to 200 ng/ml, the IL-12 has a working concentration of from 10 ng/ml to 100 ng/ml and the IL-15 has a working concentration of from 10 ng/ml to 100 ng/ml. The type I NKT cells may be derived from PBMCs, purified CD3+T cells or purified NKT cells. And the medium for the amplification of the type I NKT cells may be X-VIVO-15 serum-free medium or RPMI1640 medium containing 10% FBS or autoserum, and the RPMI1640 medium containing 10% FBS or autoserum is used for the induction of the DCs.

The present invention has the following beneficial effects: the existing NKT cell amplification technology mainly amplifies NKT cells by a fixed "stimulant+cytokine" mode and cannot specifically amplify type I or type II NKT cells, and therefore cannot fully exert their respective advantages. However, the present invention employs a "specific stimulant+staged cytokine" mode which is characterized in that: a specific stimulant α-GalCer is used to advantageously amplify the type I NKT cells, and specific cytokines IL-2, IL-7, IL-12 and IL-15 are added in a certain order at different stages of cell culture according to the characteristics of each growth stage of cells and the functional characteristics of various cytokines. Therefore, this can achieve the purposes of greatly amplifying the cells and improving their level of excreting effector cytokines and their killing activity to fully exert their anti-tumor and anti-infective function. In addition, throughout the NKT culture cycle, α-GalCer-loaded DCs or other artificially modified DC-like antigen presenting cells (APC) are added respectively on the $7^{th}$ day and the $14^{th}$ day of culture to efficiently stimulate continuous proliferation of the type I NKT cells. The NKT cell amplification method of the present invention is simple to operate and suitable for large-scale production of the type I NKT cells.

DETAILED DESCRIPTION OF THE INVENTION

Figure 1:
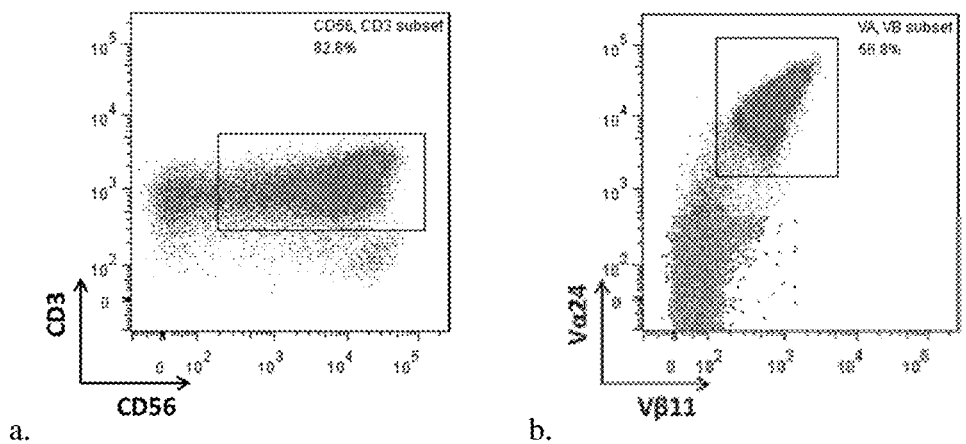
FIG. 1 is a schematic view showing the proportion of target cells in amplification products in Example 3, in which FIG. a shows the proportion of CD3+CD56+ cells and FIG. b shows the proportion of iNKT cells (Vα24+Vβ11+)

The invention will be further described below in detail with reference to particular embodiments so that those skilled in the art better understand the technical solution of the invention.

Example 1: Isolation of Peripheral Blood Mononuclear Cells (PBMCs)

1. 30 ml-50 ml of human peripheral blood anticoagulated by heparin was placed in a centrifuge tube. The peripheral blood was diluted with normal saline in a ratio of 1:1 and evenly mixed.

2. 15 ml of a lymphocyte isolation solution (ficoll) was added to a new 50 mL centrifuge tube, then the evenly mixed dilution of blood solution was slowly added to an upper layer of ficoll along the tube wall in a volume ratio of ficoll to the dilution of blood solution of 1:2 to form a clear separation therebetween, and the resulting solution was centrifuged at 3000 rpm for 30 min.

3. After centrifugation was completed, a mononuclear cell layer was transferred into a new 50 ml centrifuge tube and washed once with 30 ml of X-VIVO-15 medium, then was centrifuged at 800 g for 5 min, and the supernatant was discarded.

4. 20 ml X-VIVO-15 medium was added, the resulting mixture was evenly mixed by blowing and suction, then centrifuged at 200 g at room temperature for 10 min, and the supernatant was discarded. 10 ml X-VIVO-15 medium was added for resuspending and cell counting.

Example 2: Induced Differentiation of Dendritic Cells (DCs) for Stimulating Proliferation of Type I NKT Cells 1. The concentration of above PBMCs was adjusted to $1 \times 10^6$ cells/ml with RPMI1640 medium containing 10% FBS, and the PBMCs were placed in a T25 cell culture flask, and statically cultured for 1 h at 37° C. and 5% $CO_2$.

2. The culture flask was taken out, and the supernatant and non-adherent cells were removed. Cell surfaces were washed twice with the RPMI1640 medium containing 10% FBS, then 5 ml of the RPMI1640 medium containing 10% FBS was added, and cytokines GM-CSF and IL-4 were added at working concentrations of 500 U/ml and 50 ng/ml, respectively.

3. On the $4^{th}$ day of culture, 3 ml of a medium containing GM-CSF and IL-4 with the above working concentrations was added to the culture system.

4. On the $6^{th}$ day of culture, α-Galcer was added to the culture system with the working concentration of 100 ng/ml.

5. On the $7^{th}$ day of culture, cells were collected.

Example 3: In-Vitro Amplification of NKT Cells with High Killing Activity

1. The concentration of PBMCs was adjusted to $3 \times 10^6$ cells/ml with X-VIVO-15 cell medium, α-GalCer was added to a working concentration of 100 ng/ml, and the PBMCs were placed in a 6-well plate.

2. On the $3^{rd}$ day of culture, the culture system was refilled with X-VIVO-15 cell medium containing α-GalCer with the above working concentration.

3. On the $7^{th}$ day of culture, the α-GalCer-loaded DCs (about $1 \times 10^5$ cells) prepared in Example 2 were added to the NKT cell culture system, and stimulating factors were added to the following working concentrations: 100 ng/ml for α-GalCer, 100 U/ml for IL-2 and 20 ng/ml for IL-7. In addition, another tube of PBMCs was thawed out for inducing differentiation of DCs to re-stimulate NKT cells, and the procedure is the same as in Example 2.

4. On the $10^{th}$ day of culture, the culture medium was refilled, and α-GalCer, IL-2 and IL-7 were added to their respective working concentrations.

5. On the $14^{th}$ day of culture, the α-GalCer-loaded DCs were re-added to the NKT cell culture system while adding the stimulating factors α-GalCer, IL-2 and IL-7 to their respective working concentrations, and IL-15 was added to the culture system with the concentration of 20 ng/ml.

6. On the $17^{th}$ day of culture, the culture medium was refilled, and α-GalCer, IL-2, IL-7 and IL-15 were added to their respective working concentrations.

7. On the $20^{th}$ day of culture, the culture medium was refilled, and α-GalCer, IL-2, IL-7 and IL-15 were added to their respective working concentrations, and furthermore, IL-12 was added to a working concentration of 20 ng/ml.

8. On the 21$^{st}$ day of culture, cells were collected. 100 ul of the cell products were taken out, and the following fluorescent antibodies were added to the cells: anti-TCR Vα-PE (Beckman Coulter, clone #C15), anti-TCR Vβ-FITC (Beckman Coulter, clone #C21), anti-CD3-PB (BD Pharmingen, clone #SP34-2) and anti-CD56-PE-Cy7 (BD Pharmingen, clone #NCAM16.2). The cell products were incubated at 4° C. for 30 min, and the proportion of target cell populations in the products was detected by flow cytometry. As shown in FIG. 1, the amplification products were mainly CD3+CD56+NKT cell populations and the proportion of type I NKT cells could reach about 56.8%.

Example 4: Influence of the Addition Time of Cytokines IL-2 and IL-7 on Amplification Effects NKT cells of four groups A, B, C and D cultured by different methods under the same culture conditions (37° C., 5% $CO_2$ concentration) were tested for effects, respectively. In the four groups, α-GalCer was added at the beginning of culture until the end of the culture. In group A, IL-2 was also added at the beginning of culture. In group B, IL-2 and IL-7 were also added at the beginning of culture. In group C, IL-2 and IL-7 were added on the 3$^{rd}$ day of culture. In group D, IL-2 and IL-7 were added on the 7$^{th}$ day of culture.

Figure 2:
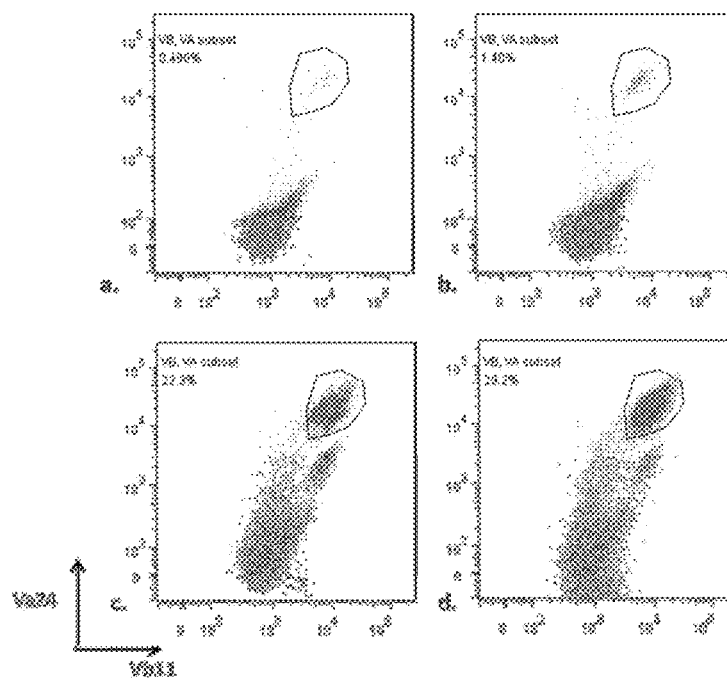
FIG. 2 is a schematic view showing the influence of the addition time of cytokines IL-2 and IL-7 on the proportion of amplification products of type I NKT cells in Example 4, in which a, b, c and d correspond to the experimental results of four groups A, B, C and D, respectively.

On the 21$^{st}$ day of culture, 100 ul of the NKT cell products amplified by the four methods A, B, C and D were respectively taken out, and the following fluorescent antibodies were added: TCR Vα-PE and TCR Vβ-FITC; and the cell products were incubated at 4° C. for 30 min, and the proportion of target cell populations in the products was detected by flow cytometry. As shown in FIG. 2, the proportion of type I NKT cells in the culture products of groups A, B, C and D gradually increased, proving that the addition of the cytokines IL-2 and IL-7 on the 7$^{th}$ day could advantageously amplify the type I NKT cells and significantly improve the purity of the type I NKT cells in the NKT amplification products.

Example 5: Influence of the Addition Time of Cytokine IL-15 on the Proportion of Amplification Products of NKT Cells NKT cells of four groups A, B, C and D cultured by different methods under the same culture conditions (37° C., 5% $CO_2$ concentration) were tested for effects, respectively. In the four groups, α-GalCer was added at the beginning of culture, and IL-2 and IL-7 were added on the 7$^{th}$ day of culture until the end of the culture. In group A, IL-15 was not added. In group B, IL-15 was also added at the beginning of culture. In group C, IL-15 was added on the 7$^{th}$ day of culture. In group D, IL-15 was added on the 14$^{th}$ day of culture.

Figure 3:
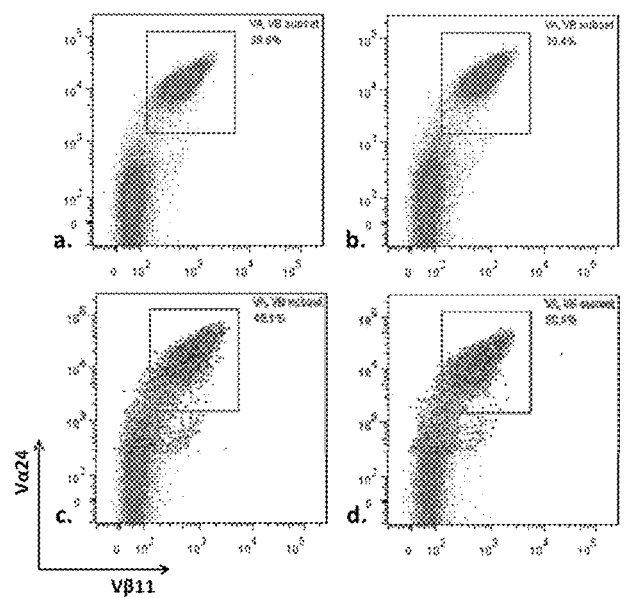
FIG. 3 is a schematic view showing the influence of the addition time of a cytokine IL-15 on the proportion of amplification products of type I NKT cells in Example 5, in which a, b, c and d correspond to the experimental results of four groups A, B, C and D, respectively.

On the 21$^{st}$ day of culture, 100 ul of the NKT cell products amplified by the four methods A, B, C and D were respectively taken out, and the following fluorescent antibodies were added: anti-TCR Vα-PE, anti-TCR Vβ-FITC, anti-CD3-PB and anti-CD56-PE-Cy7; and the cell products were incubated at 4° C. for 30 min, and the proportion of target cell populations in the products was detected by flow cytometry. As shown in FIG. 3, the proportion of type I NKT cells in the culture products of group D was superior to the other three groups.

Example 6: Influence of the Addition Time of IL-15 on the Ability of Amplification Products of NKT Cells to Secrete Cytokines The existing study results show that the ability of NKT cells to secrete Th1-type cytokines is positively correlated with their anti-tumor ability. Accordingly, in the present application, the ratio of the content of IFN-γ to the content of IL-4 in the supernatant of amplification products was detected as one of the indicators for evaluating the effector functions of the amplification products.

The ratio of IFN-γ to IL-4 in the four cell culture supernatants of Example 5 was detected by CBA (Cytometric Bead Array, cytokine microsphere detection technology) to evaluate the ability of amplification products of NKT cells to secrete effector cytokines. The results are shown in Table 1.

TABLE 1 influence of the addition time of IL-15 on the ability of amplification products of NKT cells to secrete cytokines

|  | Group A | Group B | Group C | Group D |
|---|---|---|---|---|
| IFN-γ (pg/ml) | >5000 | >5000 | >5000 | >5000 |
| IL-4 (pg/ml) | 4.47 | 3.21 | 3.07 | 1.84 |
| IFN-γ:IL-4 | >1118 | >1558 | >1629 | >2717 |

The results show that the addition of IL-15 on the 14$^{th}$ day can significantly increase the ratio of IFN-γ to IL-4 in the supernatant of the amplification products, thereby improving the ability of the amplification products to secrete effector cytokines.

Example 7: Influence of the Addition Time of Cytokine IL-15 on the Killing Ability of Amplification Products of NKT Cells Lactate dehydrogenase (LDH) is a stable cytoplasmic enzyme that is released extracellularly upon cell lysis and catalyzes its substrate tetrazolium salt (INT) to produce a red product, wherein the amount of the red product is directly proportional to the cell lysis amount. In the present application, the ability of amplified NKT cell products to kill target cells was evaluated by detecting the amount of INT in the killing system. This part was detected by an LDH detection kit (Cat. No. CK12, Dojindo) and operated according to the kit instructions.

Target cells K562 were centrifuged and the density of the target cells was adjusted to $1\times10^5$ cells/ml. The NKT cells of groups A and D cultured by different methods in Example 5 were collected by centrifugation such that the effector-to-target ratio was 5:1, 10:1 and 20:1, respectively. Three duplicate wells were set for each group. The target cells were incubated in an incubator at 37° C. and 5% $CO_2$ for 4 h. After the precipitate was fully dissolved, the absorbance was detected by an enzyme-linked immune detector and the killing rate was calculated. The results are shown in Table 2. The formula for calculating the killing rate is as follows: killing rate (%)=(OD490$_{experimental\ well}$−OD490$_{negative\ well}$)/(OD490$_{positive\ well}$−OD490$_{negative\ well}$)×100%. The comparison results are shown in Table 2.

TABLE 2 influence of cytokine IL-15 on the killing ability
of amplification products of NKT cells

| | Effector-to-target ratio | | |
|---|---|---|---|
| | 5:1 | 10:1 | 20:1 |
| Group A | 12.41 | 24.1 | 37.09 |
| Group D | 32.34 | 46.71 | 58.75 |

The results show that the addition of IL-15 on the 14$^{th}$ day of culture can significantly improve the killing ability of amplification products of NKT cells.

Example 8: Influence of the Addition Time of Cytokine IL-12 on the Proportion of Type I NKT Cells in Amplification Products NKT cells of four groups A, B, C and D cultured by different methods under the same culture conditions (37° C., 5% $CO_2$ concentration) were tested for effects, respectively. In the four groups, α-GalCer was added at the beginning of culture, IL-2 and IL-7 were added on the 7$^{th}$ day of culture, and IL-15 was added on the 14th day of culture until the end of the culture. In group A, IL-12 was not added. In group B, IL-12 was also added at the beginning of culture. In group C, IL-12 was added on the 7$^{th}$ day of culture. In group D, IL-12 was added on the 20$^{th}$ day of culture.

Figure 4:
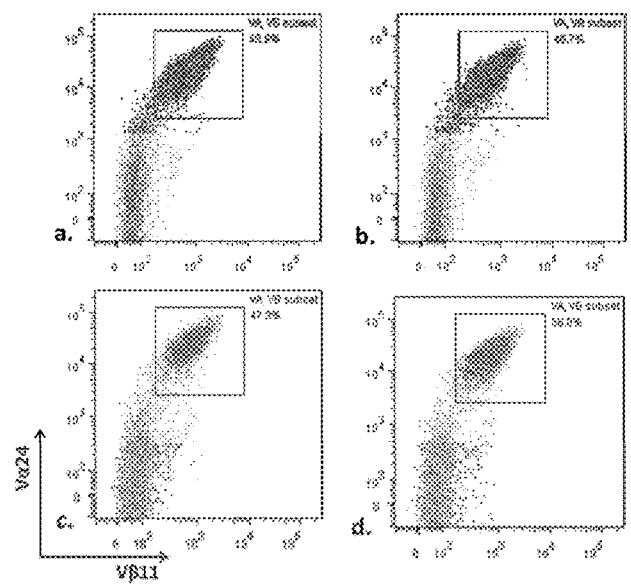
FIG. 4 is a schematic view showing the influence of the addition time of a cytokine IL-12 on the proportion of amplification products of type I NKT cells in Example 8, in which a, b, c and d correspond to the experimental results of four groups A, B, C and D, respectively.

On the 21$^{st}$ day of culture, 100 ul of the NKT cell products amplified by the four methods A, B, C and D were respectively taken out, and the following fluorescent antibodies were added: TCR Vα-PE and TCR Vβ-FITC; and the cell products were incubated at 4° C. for 30 min, and the proportion of target cell populations in the products was detected by flow cytometry. As shown in FIG. 4, the proportion of type I NKT cells in the culture products of group D was superior to the other three groups, and the addition of IL-12 too early reduced the proportion of the type I NKT cells in the amplification products, indicating that IL-12 should be added in the later stage of the culture if necessary.

Example 9: Influence of the Addition Time of Cytokine IL-12 on the Killing Ability of Amplification Products of NKT Cells Target cells K562 were taken to detect the killing ability of the cells of groups A and D in Example 8. The results are shown in Table 3.

TABLE 3 influence of cytokine IL-12 on the killing ability
of amplification products of NKT cells

| | Effector-to-target ratio | | |
|---|---|---|---|
| | 5:1 | 10:1 | 20:1 |
| Group A | 10.36 | 19.78 | 33.92 |
| Group D | 42.19 | 60.57 | 63.71 |

The results show that the addition of IL-12 on the 20$^{th}$ day of culture can significantly improve the killing ability of amplification products of NKT cells.

The basic principles, main features and advantages of the invention have been illustrated and described above. Those skilled in the art should understand that the invention is not limited to the above examples, merely the principles of the invention are described in the above examples and the description, various changes and improvements can also be made to the invention without departing from the spirit and scope of the invention, and these changes and improvements shall fall within the claimed scope of the invention. The claimed scope of the invention is defined by the appended claims and equivalents thereof.

The invention claimed is:

1. A method for improving the killing ability of amplification product of type I NKT cells in vitro, the method comprising two culture stages, wherein the first culture stage focuses on specific amplification of the number of the type I NKT cells, and the second culture stage is to synchronously perform amplification of the number of the type I NKT cells and guide directed function differentiation, comprising the following steps:
 (1) conducting specific amplification of the number of the type I NKT cells by carrying out the following steps:
  resuspending and adjusting the concentration of peripheral blood mononuclear cells (PBMCs) to form a type I NKT cell culture system, and, on day 1, adding α-GalCer to the type I NKT cell culture system to culture the type I NKT cells;
 (2) synchronously performing amplification of the number of the type I NKT cells and guide directed function differentiation by carrying out the following steps:
  on the 7th day of culture, adding α-GalCer-loaded CD1d-expressing cells to the type I NKT cell culture system while adding IL-2 and IL-7, and maintaining the concentration of α-GalCer in the type I NKT cell culture system unchanged relative to its concentration on day 1;
  on the 14th day of culture, adding an additional amount of the α-GalCer-loaded CD1d-expressing cells to the type I NKT cell culture system while adding IL-15, and maintaining the concentrations of α-GalCer, IL-2 and IL-7 in the type I NKT cell culture system unchanged relative to their respective concentrations on day 7; and
  on the 20th day of culture, adding IL-12 to the culture system while maintaining the concentrations of α-GalCer, IL-2, IL-7 and IL-15 in the type I NKT cell culture system unchanged relative to their respective concentrations on day 14, and collecting cells on the 21st day of culture.

2. The method according to claim 1, wherein the CD1d-expressing cells comprise dendritic cells (DCs), other cells capable of expressing CD1d and/or other artificially modified DC-like antigen presenting cells.

3. The method according to claim 2, wherein the α-GalCer-loaded CD1d-expressing cells are α-GalCer-loaded dendritic cells (DCs), and the α-GalCer-loaded DCs are prepared by resuspending and adjusting the concentration of PBMCs, adding IL-4 and GM-CSF at working concentrations of 500 U/ml and 50 ng/ml respectively to induce differentiation of DCs, and on the 6th day of culture, adding α-GalCer to the DCs culture system for pre-incubation for 24 h.

4. The method according to claim 1, wherein the initial concentration of the PBMCs for culturing the type I NKT cells is from $5 \times 10^5$ cells/ml to $3 \times 10^6$ cells/ml and the initial concentration of the PBMCs for inducing the differentiation of the DCs is from $1 \times 10^6$ cells/ml to $5 \times 10^6$ cells/ml.

5. The method according to claim 1, wherein the α-GalCer has a working concentration of from 50 ng/ml to 500 ng/ml.

6. The method according to claim 1, wherein the IL-2 has a working concentration of from 10 U/ml to 100 U/ml, the TL-7 has a working concentration of from 20 ng/ml to 200 ng/ml, the IL-12 has a working concentration of from 10 ng/ml to 100 ng/ml and the IL-15 has a working concentration of from 10 ng/ml to 100 ng/ml.

7. The method according to claim 1, further comprising refilling the type I NKT cell culture system with a culture medium every 2 to 3 days.

8. The method according to claim 7, wherein the culture medium comprises X-VIVO-15 serum-free medium or RPMI1640 medium containing 10% FBS or autoserum, and wherein the RPMI1640 medium containing 10% FBS or autoserum is used in the induction of the DCs.

9. The method according to claim 1, wherein the collected cells have at least 50% of type I NKT cells relative to a total amount of NKT cells in the collected cells.

* * * * *